(12) United States Patent
Kawasaki et al.

(10) Patent No.: US 7,330,745 B2
(45) Date of Patent: Feb. 12, 2008

(54) LIVING BODY PHOTOMETRIC DEVICE

(75) Inventors: Shingo Kawasaki, Chiba (JP); Naoki Tanaka, Saitama (JP)

(73) Assignees: Hitachi Medical Corporation, Tokyo (JP); Hitachi, Ltd., Tokyo (JP)

( * ) Notice: Subject to any disclaimer, the term of this patent is extended or adjusted under 35 U.S.C. 154(b) by 348 days.

(21) Appl. No.: 10/526,893

(22) PCT Filed: Sep. 5, 2003

(86) PCT No.: PCT/JP03/11359

§ 371 (c)(1),
(2), (4) Date: Mar. 4, 2005

(87) PCT Pub. No.: WO2004/021889

PCT Pub. Date: Mar. 18, 2004

(65) Prior Publication Data

US 2006/0206017 A1    Sep. 14, 2006

(30) Foreign Application Priority Data

Sep. 5, 2002  (JP) .............................. 2002-260300

(51) Int. Cl.
*A61B 5/00* (2006.01)
(52) U.S. Cl. ........................ 600/310; 600/407
(58) Field of Classification Search ................ 600/310, 600/340, 407, 473, 476
See application file for complete search history.

(56) References Cited

U.S. PATENT DOCUMENTS 5,803,909 A * 9/1998 Maki et al. .................. 600/310

(Continued)

FOREIGN PATENT DOCUMENTS

JP     09-098972    4/1997

(Continued)

OTHER PUBLICATIONS

Non-invasive assessment of language dominance with near-infrared spectroscopic mapping, Neurscience Letters 256 (1998) 49-52.

*Primary Examiner*—Eric Winakur
*Assistant Examiner*—Etsub D Berhanu
(74) *Attorney, Agent, or Firm*—Antonelli, Terry, Stout & Kraus, LLP.

(57) ABSTRACT

By making use of a set of loading of stimulation and no loading, variation signals in time of hemoglobin density at a plurality of measurement points of a subject attached of an optical measurement probe and corresponding to a plurality of channels are detected, and for the respective detected hemoglobin variation signals principal component analysis is performed as well as a representative signal having a higher contribution rate is extracted and the extracted representative signal is displayed on a monitor. A correlation between the representative signal and a task reference and response waveform representing a response pattern of a living body in response to a stimulation task is calculated, and a representative signal having the highest correlation value as calculated is displayed in a discriminable manner from the other signals as a task related signal which responds most to the stimulation given to the subject. From weights of the respective channels for the representative signal displayed as the task related signal, an optical measurement point or region, which responds most to the task is identified and displayed in discriminable manner.

25 Claims, 7 Drawing Sheets

U.S. PATENT DOCUMENTS 6,240,309 B1 * 5/2001 Yamashita et al. .......... 600/407
6,542,763 B1 * 4/2003 Yamashita et al. .......... 600/310
6,901,284 B1 * 5/2005 Maki et al. ................. 600/476

FOREIGN PATENT DOCUMENTS

| JP | 09-231366 | 9/1997 |
|---|---|---|
| JP | 11-311599 | 11/1999 |
| JP | 2000-237194 | 9/2000 |
| JP | 2001-336975 | 12/2001 |
| JP | 2002-522837 | 7/2002 |
| WO | WO 00/10059 | 2/2000 |
| WO | WO 02/32317 A1 | 4/2002 |

* cited by examiner

LIVING BODY PHOTOMETRIC DEVICE

FIELD OF THE INVENTION

The present invention relates to a living body photometric apparatus, which measures information inside a living body by making use of light beams and more specifically, relates to a living body photometric apparatus, which can specify accurately and easily a reactive portion inside the living body when a task load is given to the living body.

CONVENTIONAL ART

A living body photometric apparatus is an apparatus in which light beams having wavelength from visible region to infrared region are irradiated to a living body and reflected or scattered light beams inside the living body are detected so as to measure information inside the living body, and with which blood circulation and blood circulation dynamics inside the living body, moreover, variation in time of light absorption materials in blood such as hemoglobin can be easily measured with less restriction to a subject and without giving any harms to the subject. Thus clinical application of the living body photometric apparatus is expected.

In the living body photometric apparatus, the measurement result is displayed such as in a graph representing hemoglobin density variation in time at a measurement position (time course representation) and in a contour imaging (topography) of a spatial distribution variation of hemoglobin at a measurement region. Further, the measurement result is displayed as an image in a color phase such as red and blue assigned to spatial distribution of hemoglobin and variation in time thereof.

Examples of clinical applications of the living body photometric apparatus are such as local focus identification of epilepsy and language area region identification examination as presurgical examination of epilepsy therapy. The language area region identification examination is a very important examination suppressing damage low for brain function tissue at the time when removing the local focus portion of epilepsy and is required to correctly specify the region.

The language area region identification examination by making use of the living body photometric apparatus is, for example, disclosed in E. Watanabe et al., "Non-invasive assessment of language dominance with near-infrared spectroscopic mapping" Neuroscience Letters 256 (1998) 49-52, in which hemoglobin variation signals are measured from a plurality of positions for each of the right and left temporal lobes while giving a subject language stimulus loads, the obtained plurality of hemoglobin variation signals are added and averaged for every right and left temporal lobes and through comparison of these averaged values the language area region is identified.

Further, such as the present applicants are now developing a living body photometric apparatus, which improves convenience in living body photometry and objectivity in measurement and is suitable for the language area region identification (see JP 11-311599 A and WO 02/32317 A1)

As has been explained above, for identification of an active region in the brain such as the language area region identification, it is important to diagnose a correct position thereof, and the living body photometric apparatus is required to provide correct information and information facilitating diagnosis.

However, when performing examination for specifying the small language area region of about 3 cm×3 cm, since in the hemoglobin variation signals measured other signals than activation signals in the brain brought about by a load for the language area region identification, for example, signals due to hand motion for writing letters and further, signals due to such as the sense of sight and the sense of hearing are contained, the diagnosis accuracy of the method of specifying the active portion brought about by the loading through average value comparison of the signals of right and left temporal lobes is not high and remains in about 60%. For this reason, in the region specifying examination by making use of the living body photometric apparatus, the apparatus is desired to be able to specify a small region as well as to be able to improve diagnosis accuracy.

Further, with the conventional display method in the living body photometric apparatus such as the time course representation of hemoglobin variation signals for every measurement channel and the topography representation, it was sometimes difficult to easily grasp a specific active region.

Accordingly, an object of the present invention is to provide a living body photometric apparatus, which can accurately specify an objective small active region in a brain from hemoglobin variation signals measured.

SUMMARY OF THE INVENTION

In order to achieve the above object, the present invention is characterized in that a signal processing portion of the living body photometric apparatus is added of a function, which performs a principal component analysis for signals measured. The principal component analysis function is understood to be able to extract from the signals measured only signals corresponding to the loaded task. Thereby, an apparatus, which permits to effectively compare interregional signal intensity and to accurately identify an active portion in the brain in a clinical examination application such as the language area region identification.

Namely, the living body photometric apparatus according to the present invention comprises a light measurement portion which measures intensity of passing light at a plurality of measurement points of a subject and outputs signals corresponding to intensity of passing light for every measurement point as measurement data for every measurement channel, a signal processing portion which processes the measurement data output from the light measurement portion and images a living body reaction when a predetermined task is given to the subject and an input and output portion which displays a processed result of the signal processing portion as well as sends a command necessary for a processing in the signal processing portion, characterized in that the signal processing portion includes means for performing a principal component analysis for the measurement data and for extracting a representative signal which most reflects the living body reaction when the task is given.

Specifically, the signal processing portion performs a principal component analysis for the measured data, calculates not less than one representative signal and weight of the representative signal for every measurement channel, correlates the representative signal with a referential response signal representing a passing light pattern when the task is given and extracts a representative signal reflecting most the living body reaction when the task is given among the representative signals as a task related signal.

According to the living body photometric apparatus of the present invention, since the representative signal reflecting most of the living body reaction when the task is given can be extracted as the task related signal, through comparison of the weight of the task related signal for every measurement channel, namely comparison of abundance frequency, an active portion which reacts most with respect to the task (language area when the task is language stimulus) can be accurately specified.

The present invention further provides a living body photometric apparatus with an improved display function. Namely, the living body photometric apparatus according to the present invention is characterized in that the input and output portion is adapted to display a waveform of the representative signal calculated through the principal component analysis in the signal processing portion and the weight of the representative signal for every measurement channel. Further, the living body photometric apparatus according to the present invention is characterized in that the calculated result of the correlation between the representative signal and the referential response signal is displayed together with the waveform of the representative signal.

According to the present living body photometric apparatus, from a screen on which the waveform of the representative signal is displayed, a user can discriminate among the representative signals the task related signal which is a representative signal showing the highest correlation with the referential response signal, and further, from the weight of the task related signal for each measurement channel, the user can discriminate a most reactive portion (a concerned measurement channel) to the task.

In a further preferable living body photometric apparatus according to the present invention, the signal processing portion receives a condition for the task from the input and output portion and prepares a referential response signal depending on the condition. According to the present living body photometric apparatus, since a referential response signal of a suitable reaction pattern depending on the task can be used, correctness when extracting the task related signal is improved.

In a still further preferable living body photometric apparatus according to the present invention, the signal processing portion divides the measurement channels into a plurality of groups, calculates average values of the weights of each measurement channel for every groups with respect to the representative signal selected as the task related signal and further calculates from the average values dominance of the response with regard to the task in the groups thereby to display the same.

DETAILED DESCRIPTION OF THE EMBODIMENT

Herein below an embodiment of the present invention will be explained in detail. In the explanation below, as an object of light measurement, amount of hemoglobin (including oxy hemoglobin, deoxy hemoglobin and total hemoglobin) in a living body is referred to, however, in the living body photometric apparatus according to the present invention, substances such as cytochrome other that the hemoglobin which absorb light beams of near infrared region can be used as the measurement object.

Figure 1:
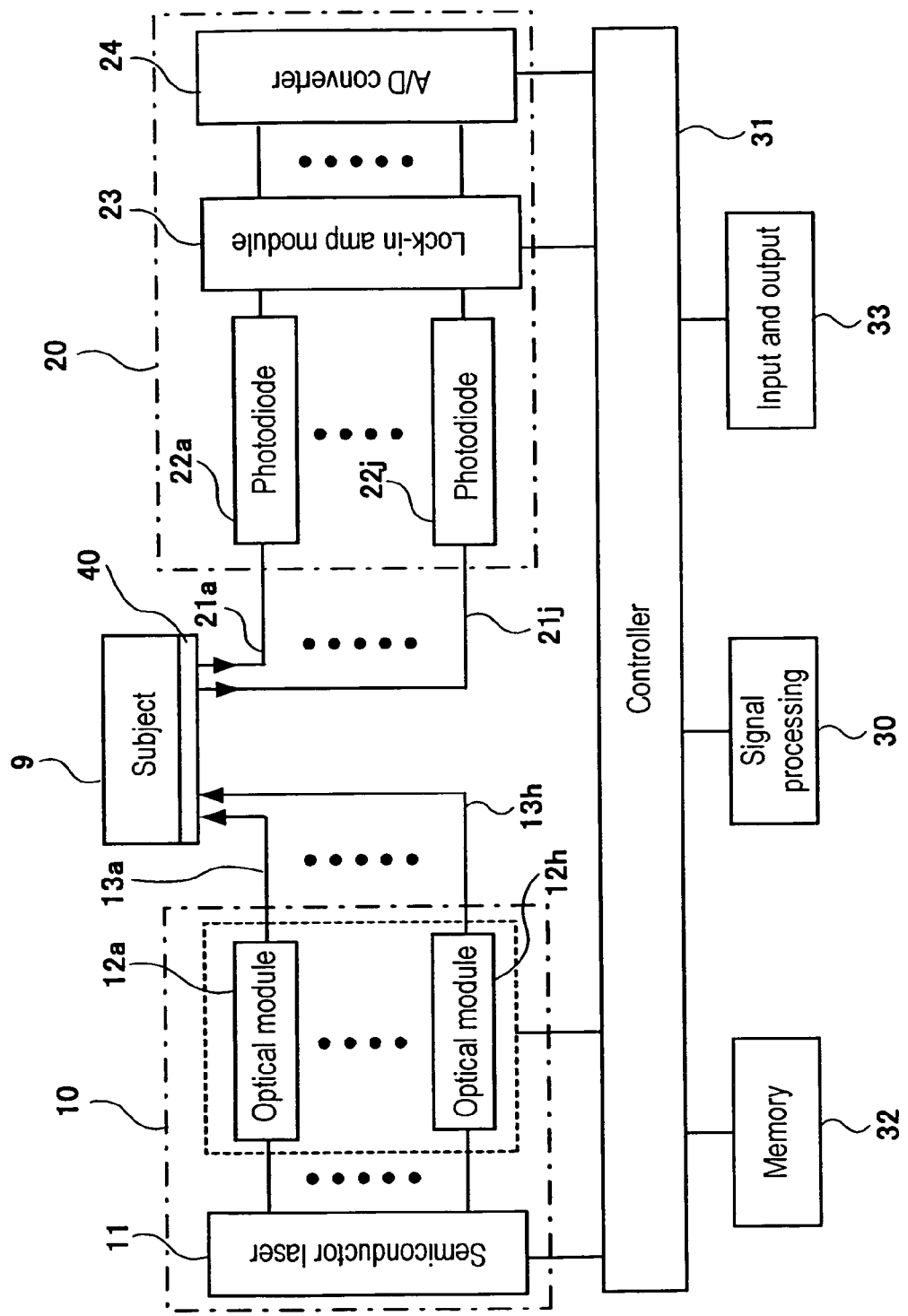
FIG. 1 is a block diagram showing a schematic entire structure of a living body photometric apparatus according to the present invention.

FIG. 1 is a block diagram showing a schematic entire structure of a living body photometric apparatus according to the present invention. The living body photometric apparatus is provided with a light source 10 which irradiates near infrared light beams to a living body, an optical measurement portion 20 which measures light passed through the living body and converts the same into an electrical signal and a signal processing portion 30 which calculates living body information, more specifically, hemoglobin density variation in blood at a measurement portion based on the signals from the optical measurement portion 20 and displays the result. Further, in order to contact an end of an optical fiber to a measurement position of a subject for transmitting light beams from the light source 10 as well as to contact an end of another optical fiber to a measurement position of the subject for detecting light beams passed (including scattered) inside the living body and for transmitting the same to the optical measurement portion 20, the living body photometric apparatus is provided with an attachment member 40 for securing the ends of these optical fibers at predetermined positions. Herein below, the attachment member and the end portions of the optical fibers secured to the attachment member will be called inclusively as a probe 300.

The light source 10 is constituted by semiconductor lasers 11, which respectively emit light beams having a plurality of wavelengths (synonym of frequency) in a region from visible to near infrared, for example, wavelengths of 780 nm and 830 nm, a plurality of optical modules 12 provided with modulators for modulating the light beams of the two wavelengths into a plurality of different frequencies and a plurality of irradiation use optical fibers 13, which guide the light beams output from the optical modules 12 to the probe. The light beams of the two frequencies irradiated from the semiconductor lasers 11 are mixed and input in respective optical modules 12 wherein the same are modulated in different frequencies in every optical modules, and the modulated light beams of the two frequencies are irradiated to the respective examination portions of the subject via the respective irradiation use optical fibers.

The optical measurement portion 20 is connected to detection use optical fibers 21 and is constituted by photoelectric conversion elements such as photo diodes 22 which convert the amount of the light beams transmitted by the respective detection use optical fibers 21 to respective corresponding electrical signals, lock-in amplifier modules 23 to which the electrical signals from the photo diodes 22 are input and from which selectively output signals corresponding to respective irradiation positions and detection positions as well as the frequencies and an A/D converter 24 which A/D converts the signals output from the lock-in amplifier modules 23. Number of lock-in amplifier modules 23 to be provided is at least the same number of the signals to be measured.

The probe 300 is constituted in such a manner that a matrix of proper size such as 3×3 and 4×4 with a predetermined pitch is formed on the attachment member 40 and the ends of the irradiation use optical fibers and the ends of the detection use optical fibers alternatively disposed thereon by making use of a securing use socket.

The light beams detected by the detection use optical fibers in the living body photometric apparatus are mixture of a plurality of light beams having different frequencies, which are respectively irradiated from a plurality of adjacent irradiation use optical fibers and passed inside the living body. The lock-in amplifier modules 23 selectively detect these pluralities of signals having different frequencies with reference to the irradiation positions, irradiation frequencies and detection positions thereof. Thereby, information inside the living body is detected at measurement points determined by points between the end positions of the irradiation use optical fibers and the end position of the detection use optical fibers, more specifically, the intermediate points thereof.

These measurement points correspond to the number of channels detected by the lock-in amplifier modules 23, for example, in a case of a probe having 3×3 matrix, the number of measurement points between the irradiation positions and the detection positions is 12, thus a light measurement of 12 channels can be performed.

The signal processing portion 30 is connected to the optical measurement portion 20 via a control portion (centralized processing unit: CPU) 31 for controlling the entirety of the apparatus, processes the voltage signals (digital signals) sent from the optical measurement portion 20 and performs conversion thereof into signals representing living body information, more specifically, conversion into hemoglobin variation signals representing hemoglobin density and variation thereof in time at the measurement portions and preparation of data for topography image. Other than the above referred to image preparation function, the signal processing portion 30 includes such as a function of extracting from the hemoglobin variation signals measured at the respective measurement channels signals (task related signals) representing a feature of a task (load) given to the subject at the time of the measurement and a function of calculating based on the task related signals the most reactive measurement portion (channel) with respect to the task. In order to perform these functions, the signal processing portion 30 is provided with an arithmetic unit.

The CPU 31 controls such as operations of light beam irradiation and detection, an application timing of the load (stimulus), processing including the analysis of the measured signals and preparation of images and display thereof. For this purpose a variety of softwares are assembled into the CPU 31. Further, the arithmetic function of-the signal processing portion can be borne by the CPU 31.

The living body photometric apparatus is further provided with a memory portion 32 in which digital signals sent from the optical measurement portion 20 and data of after signal processing are stored and an input and output portion 33 which displays the processed result in the signal processing portion 30 as well as permits to input necessary instructions for the measurement and signal processing. More specifically, the input and output portion 33 is provided with a input manipulation board including on/off switches, key board and mouse and a display unit of such as CRT and liquid crystal.

In the thus constituted living body photometric apparatus, the light measurement is performed in such a manner that the light beams modulated in different frequencies are irradiated from the probe 300 attached to the living body through the irradiation use optical fibers 13, the light beams passed through the living body and detected by the detection use optical fibers 21 are respectively converted into electrical signals, which are detected for every measurement point at an intermediate point between respective irradiation positions and detection positions and hemoglobin variation signals are obtained by converting the electrical signals into variation in time of the hemoglobin densities in blood at measurement portions. The hemoglobin variation signals measured at the respective measurement points are subjected to a variety of analysis in the signal processing portion and these analysis results are displayed on the monitor screen in the input and output portion 33.

Now, an example of sequences for specifying a reactive portion of the living body in response to a predetermined task in the above explained living body photometric apparatus will be explained with reference to the flowchart in FIG. 2. The following explanation is a sequence effective for identifying a language area region in presurgical examination for epilepsy.

Figure 3:
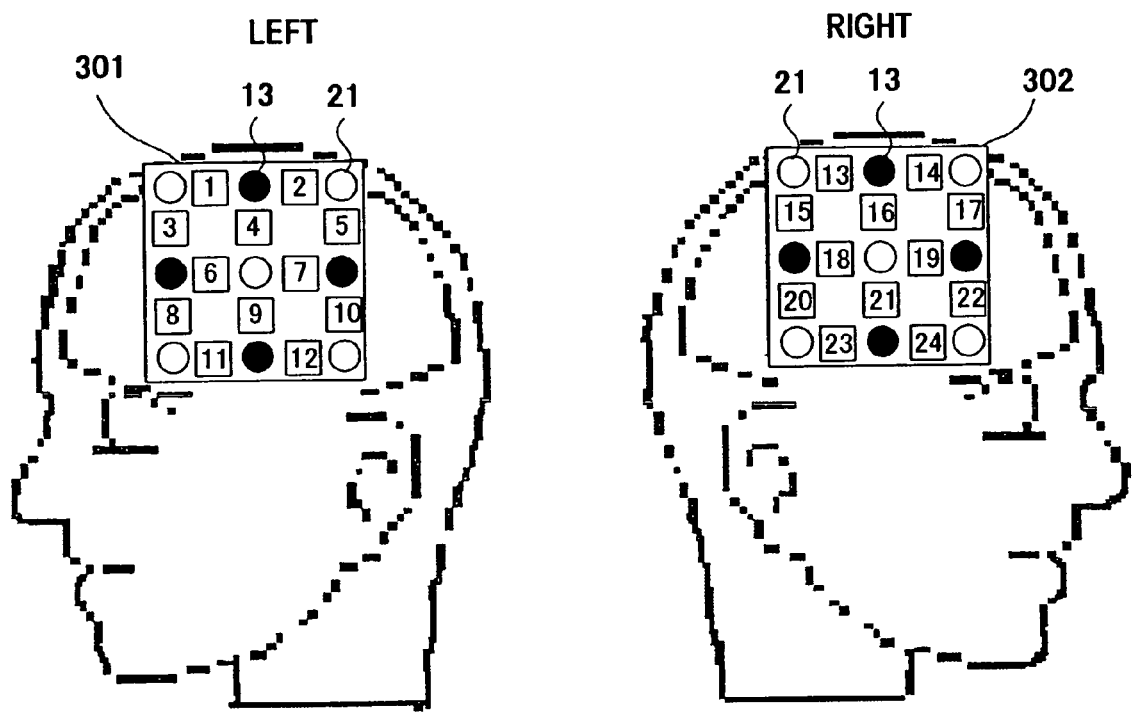
FIG. 3 is a view showing an attachment state of a probe to a subject when the measurement object is a head.

At first the probe is attached to the right and left temporal lobes of the subject (step 201). FIG. 3 shows the probe attached. As shown in the drawing, in the present embodiment, the top ends of the irradiation use optical fibers and the top ends of the detection use optical fibers are arranged in a matrix of 3×3. As has been explained previously, since the measurement points are located at the intermediate points between the arranged points of the irradiation use optical fibers and the detection use optical fibers, the number of measurement points, namely, the number of channels in the probe formed in the matrix of 3×3 of the present embodiment is 12. Probes 301 and 302, each having 12 channel measurement points, are attached respectively to the right and left temporal lobes. Further, in FIG. 3, for example, 9 total optical fibers including 4 irradiation use optical fibers and 5 detection use optical fibers are arranged at crossing points of the matrix in such a manner to sandwich the positions indicated by measurement channel numbers. Accordingly, in the case of the present embodiment in which the probe is attached to the right and left temporal lobes, 8 of the optical modules 12 and 8 of the irradiation use optical fibers 13 in the light source portion 10 and 10 of the detection use optical fibers 21 and 10 of photo diodes in the optical measurement portion 20 are required.

After completing the attachment of the probes 301 and 302 to the living body, the measurement is performed (step 202). The measurement begins to turn on a measurement switch provided at the input and output portion 33. When turning on the measurement switch, the semiconductor lasers 11 in the light source 10 are oscillated and emit light beams having different wavelengths of 780 nm and 830 nm, and the light beams having the two wavelengths are mixed and input into optical modules 12$a$, . . . 12$h$, the two light beams having 780 nm and 830 nm input into respective optical modules are modulated into different frequencies for every module by a modulator in respective optical modules. These modulated light beams are guided to the probes 301 and 302 via the irradiation use optical fibers 13$a$, . . . 13$h$ and are irradiated onto the right and left temporal lobes. The irradiated light beams pass through the skin and the skull and after repeating passing and scattering of the light beams through the fine blood vessels and tissues in the brain, the light beams input into probe side openings for the detection use optical fibers 21a, 21j. Further, since the light absorbance characteristics of oxy hemoglobin and deoxy hemoglobin are different depending on the wavelength thereof irradiated from the irradiation use optical fibers, the light amount input from the detection use optical fibers differs depending on amount of hemoglobin in blood vessels at the detection portions. The light beams input into the detection use optical fibers 21a, . . . 21j are respectively converted into electrical signals by the photo diodes 22a, . . . 22j and these electrical signals are discriminated according to the frequency thereof by the lock-in amplifier modules 23. Since the frequency of the light beams irradiated from the irradiation use optical fibers corresponds to the positions of the optical fibers and the positional relationship between the detection use optical fibers and the irradiation use optical fibers are determined, the frequencies of the signals discriminated at the lock-in amplifier modules 23 and the measurement points are coordinated. Then the signals output from the lock-in amplifier modules 23 are converted into digital signals by the A/D converter 24 and output to the signal processing portion 30 in which signal processing such as for analysis and image display is performed.

The above measurement operation is performed while giving a predetermined task (stimulation) to the subject and the hemoglobin variation signals are obtained from the subject. In the above example, since an identification of the language area is an object, stimulations for activating the language area such as a game of making word chains and writing of words having a same pronunciation are given as the task. The task can be replaced by other stimulation to five senses to the living body such as visual stimulation, olfactory stimulation, auditory stimulation and pain stimulation depending on the diagnosis object. Then the measurement is performed by combining an application period (loading period) of the language stimulation and rest period (no load period) as a set and by repeating the set in plurality of times.

The hemoglobin signals appear as difference signals between the signals measured under a condition when no load (stimulation) is given to the brain of the subject and the signals measured after applying a load and one set of difference signals is obtained from the respective channel 1 through 24 in the right and left probes 301 and 302 at the same time and is displayed. When the language stimulation is repeated, namely, a plurality set of hemoglobin variation signals are obtained in a time course, the latest information or averaging after adding the plurality set of signals for respective channels is displayed.

Figure 4:
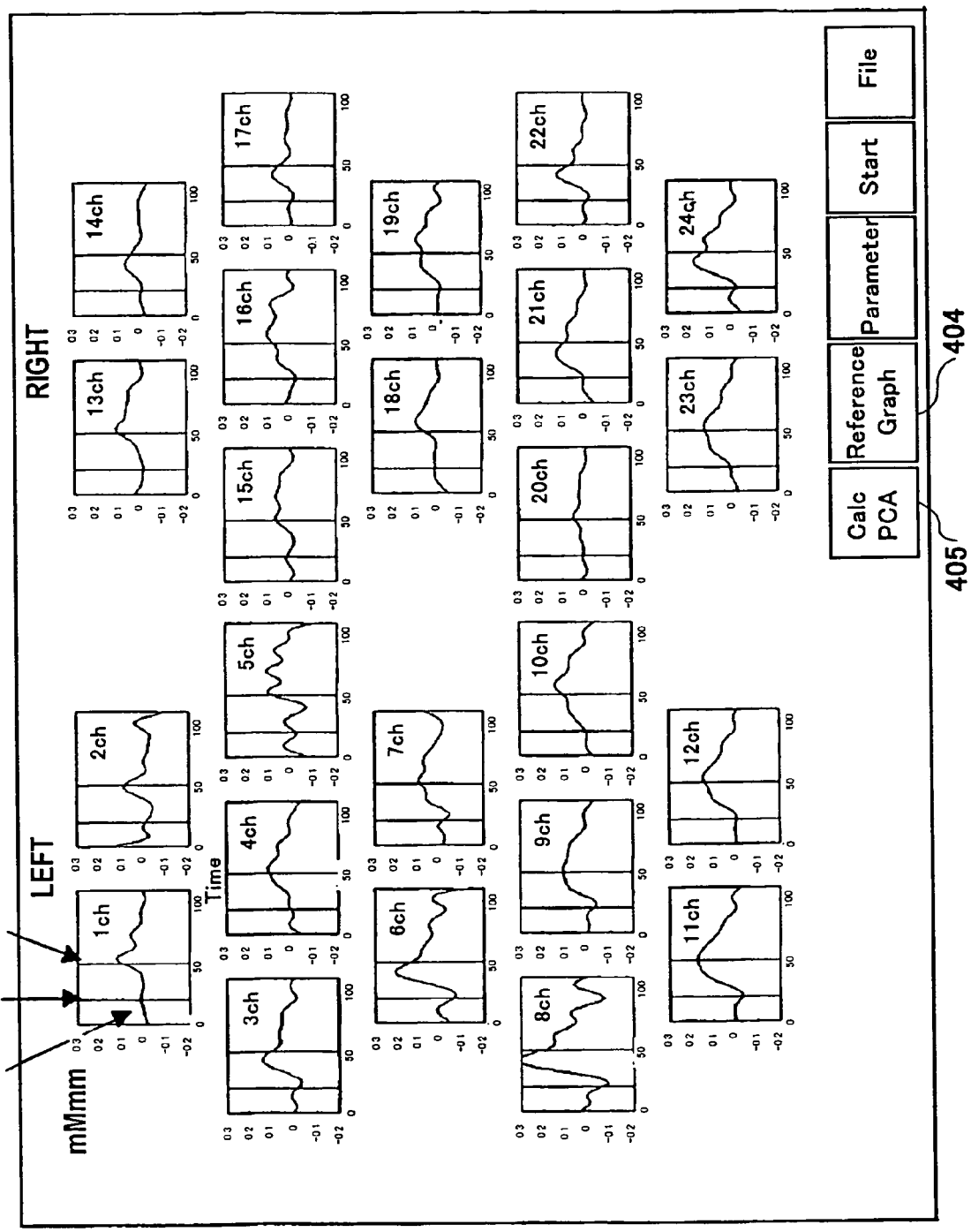
FIG. 4 is a view showing an example in which a measurement result of hemoglobin variation signal in response to a language stimulus loading is displayed on a screen.

FIG. 4 shows an example of displayed images on the monitor. As shown in the drawing, the hemoglobin variation signal 401 is displayed in a time course graph for every channel wherein abscissa is time axis and ordinate is hemoglobin density. In the graph, a stimulation start point (time) 402 and a stimulation end point (time) 403 are indicated on the ordinate. Further, on the monitor screen a variety of command input buttons such as "Calc PCA" 404 and "Reference Graph" 405 are provided in order to permit an operator to send a subsequent processing command to the control portion 31 and the signal processing portion 30. These input buttons are always displayed on the following display screens.

Figure 5:
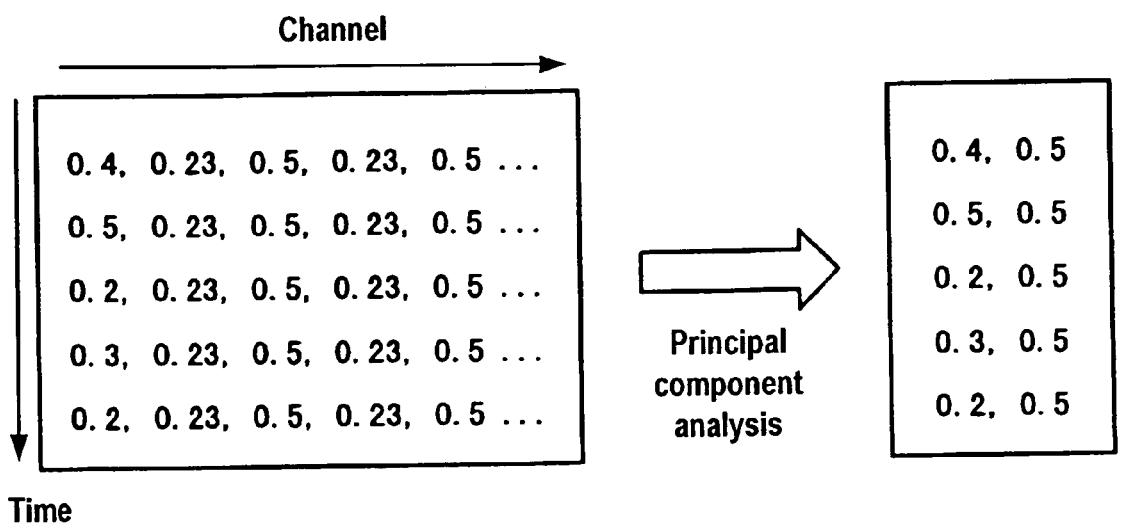
FIG. 5 is a view for explaining a principal component analysis performed for hemoglobin variation signal measured.

The signal processing portion 30 performs a principal component analysis processing for the hemoglobin variation signals of the respective channels measured in step 202. The principal component analysis processing is a known method in the field of mathematics and in the present embodiment, a pattern having high abundance frequency with respect to energy is extracted among the plurality of detected signals. In other words, some of representative signals having a contribution rate more than a predetermined contribution rate for the 24 channel hemoglobin signals measured are calculated (step 203). The principal component analysis processing is executed by clicking the "Calc PCA" button 404 on the screen in FIG. 4. The principal component analysis is a method of converting high dimensional data into further low dimensional data without losing information as much as possible and in the present embodiment, as shown in FIG. 5, with regard to a plurality of measured data of hemoglobin variation signals defined by axes of time and channel number, the dimension (24 channels) of the channel axis is compacted and is converted to data having further less channels. Further, when "Calc PCA" button 404 is clicked, the display screen is changed over from one shown in FIG. 4 to one shown in FIG. 6.

The contribution rate is an index showing how much a principal component (representative signal) extracted via the principal component analysis expresses the feature contained in the measured data and can be determined by calculating "a ratio of variance of the principal component occupying in the total variance" in the principal component analysis. In the present embodiment, a representative signal having, for example, more than 90% contribution rate is calculated.

Figure 6:
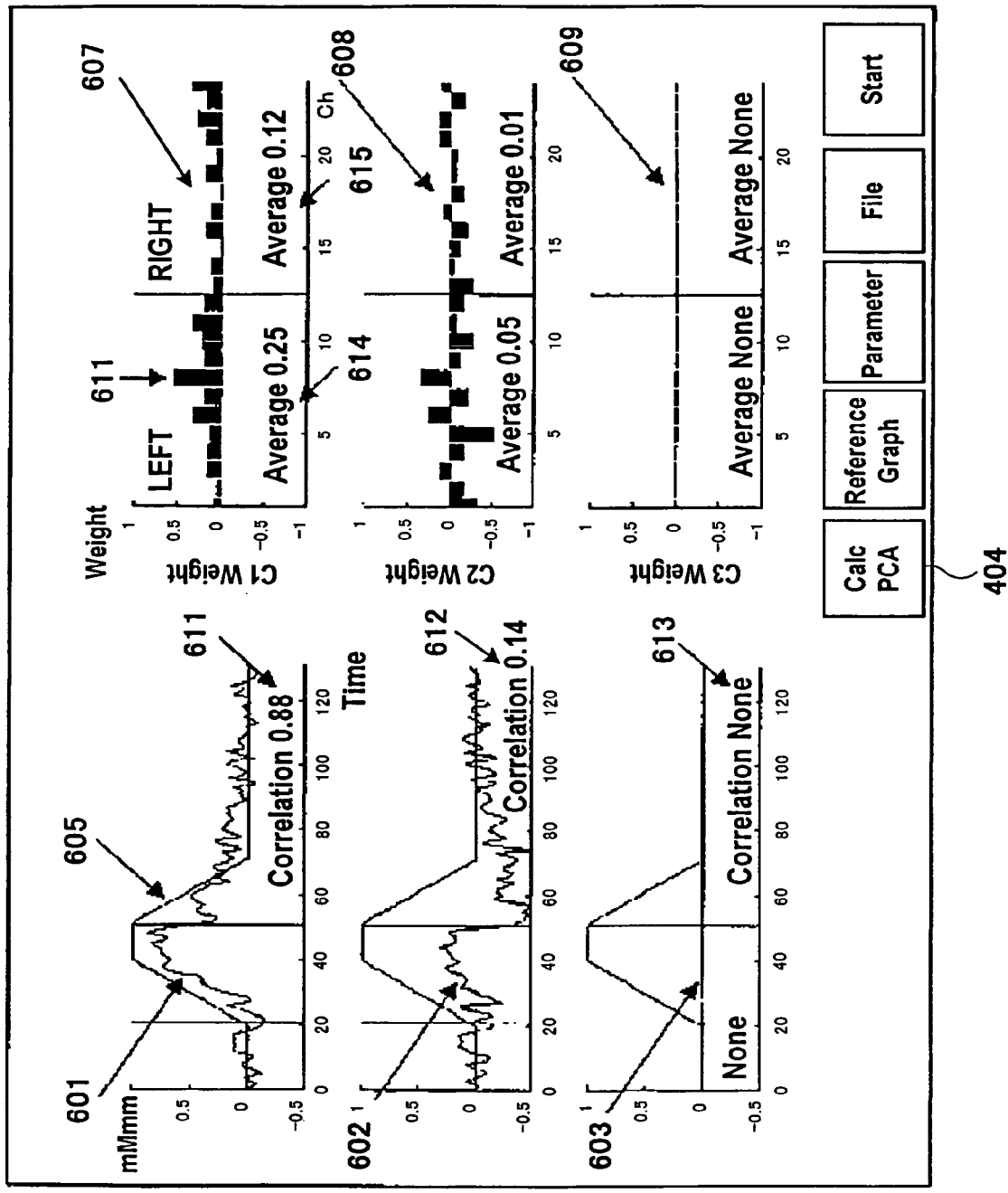
FIG. 6 is a view showing an example in which a result of the principal component analysis for the hemoglobin variation signal is displayed on the screen.

An example of images displaying the result of the principal component analysis is shown in FIG. 6. As shown in the drawing, in the present embodiment, two kinds of signals 601 and 602 are extracted and displayed as the representative signals. Since these two kinds of signals express more than 90% measurement data for all the channels, a third signal 603 is not calculated.

When calculating the representative signals by compacting the measured data with regard to the channel axis in the principal component analysis, coupling coefficients to be multiplied to the respective channels are calculated. These coupling coefficients are weights in the respective channels for the representative signals, namely, correspond to the abundance frequencies. Weights 607 and 608 for the respective channels calculated with respect to the representative signals 601 and 602 are, for example, shown in a bar graph in which abscissa is the channel number and ordinate is the weight and are displayed adjacent to the representative signals. A relationship between actual signals measured, representative signals and the weights will be explained, for example, with reference to a eighth channel, in that an added value of a value determined by multiplying the representative signal 601 with the weight for the eighth channel adjacent to the representative signal 601 and a value determined by multiplying the representative signal 602 with the weight for the eighth channel adjacent the representative signal 602 is substantially the same as the actually measured value for the eighth channel. Further, the weights displayed in the bar graph are effectively used by the operator for identifying the most reactive portion (channel) in response to the task.

Subsequently, the signal processing portion 30 correlates the calculated representative signals 601 and 602 with general hemoglobin variation signals obtained in response to a given task, in that a language stimulation and extracts a task related signal (step 205). The general hemoglobin variation signal pattern with respect to the task is one determined empirically and experimentally by making use of other modalities in the field of medical imaging diagnosis such as an MRI apparatus and a PET apparatus, and it is known, for example, that the hemoglobin variation in response to a language stimulation shows a trapezoidal pattern, in that rises in about 10 sec. from the start of the stimulation and decreases in about 10 sec. after ending the stimulation. When a task application pattern is fixed, these hemoglobin signal variation patterns can be stored beforehand in the memory portion 32, however, in the present embodiment, a case will be explained in which a user prepares a hemoglobin variation signal pattern with respect to a task in response to any application patterns to be set.

Figure 7:
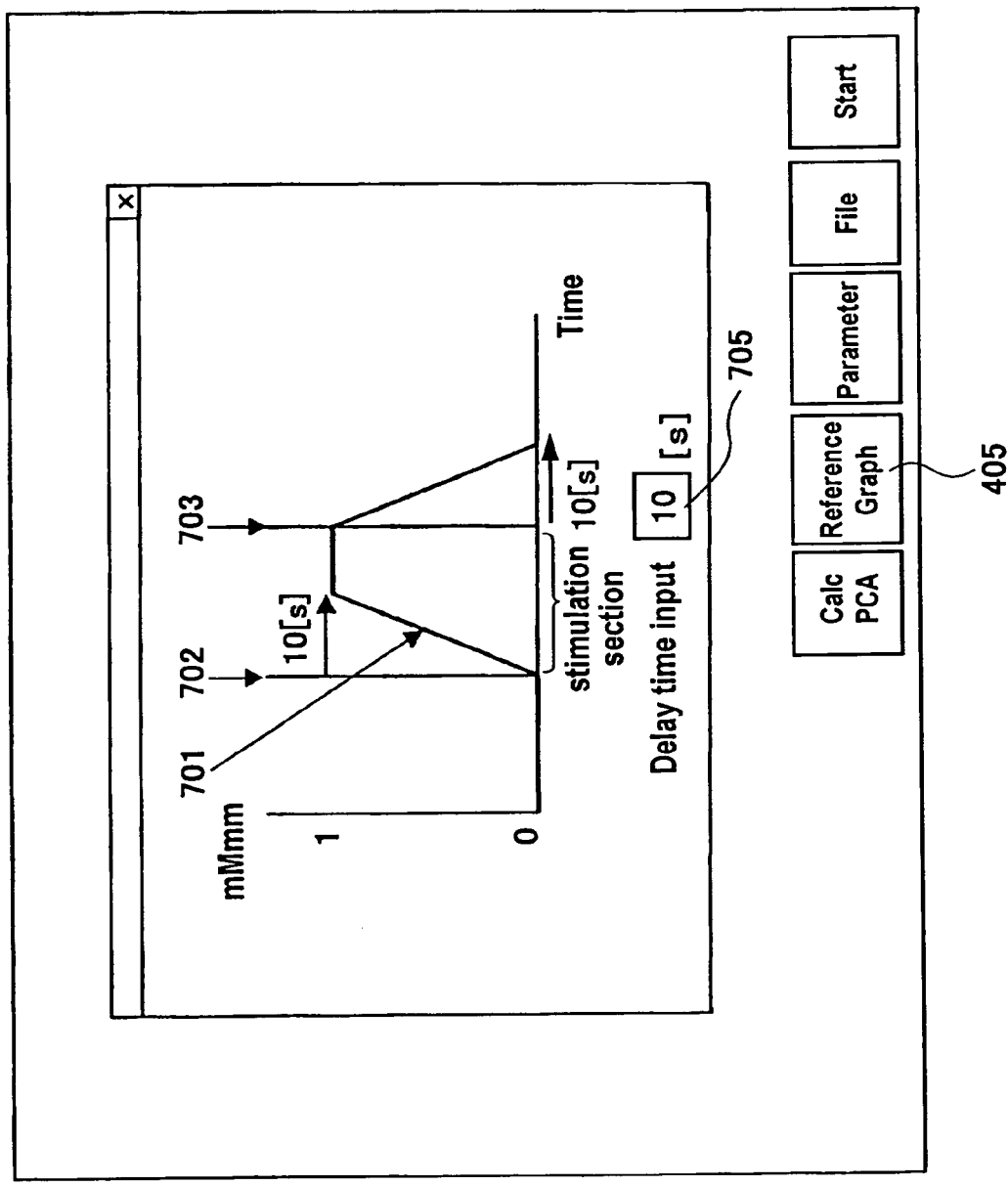
FIG. 7 is a view showing an example of a screen for preparing a referential response signal which is used for analyzing the hemoglobin variation signal.

The preparation of the hemoglobin variation signal pattern is executed at the same time when, for example, by clicking "Reference Graph" button on the screen shown in FIG. 6, the displayed image as shown in FIG. 6 is changed over to the one shown in FIG. 7 (step 204). FIG. 7 shows an example of screen images when a user prepares a language reference and response waveform 701, which is a general hemoglobin variation signal pattern with respect to language stimulation. In this screen image, a box 705 is provided for inputting a delay time from the stimulation start to the appearance of the maximum value of the hemoglobin variation and from the stimulation end to the return of the hemoglobin variation to the original state before the stimulation start, and when a delay time in response to a load is input in the box 705, a trapezoidal waveform having the delay time being input of, for example, 10 sec. is produced as the language reference and response waveform 701 with respect to a rectangular waveform having a signal value 1 at the stimulation start point 702 and the stimulation end point 703. Then, the language reference and response waveform 701 thus produced is displayed by overlapping on the graph of the representative signals 601~603 as shown in FIG. 6 (In FIG. 6, the language reference and response waveform is indicated as 605). Further, in the present embodiment, although an example of inputting a numerical value for the delay time has been shown, in another example, while assuming the rectangular waveform having signal value of 1 at the stimulation start point 702 and at the stimulation end point 703 as a figure, the delay time can be input by moving the two apexes of the rectangular in the direction of the time axis by drugging operation of a mouse. Further, since it is sufficient if the step 204 of preparing the language reference and response waveform is executed prior to the step of calculating the correlation with the representative signals, the preparation step can be performed either before the start of the measurement or after the measurement.

The calculation result of the correlation between the representative signals 601~603 and the language reference and response waveform 701, namely, the correlation value is displayed together with the graph of the representative signals. In the display example as shown in FIG. 6, the correlation values are displayed at the right end portions of the graphs of the representative signals as 611, 612 and 613. When observing the display result, the correlation value between the representative signal 601 and the language reference and response waveform 701 shows as 0.88 and the correlation value between the representative signal 602 and the language reference and response waveform 701 shows as 0.14, therefore, it is understood that among the two representative signals the representative signal 601 having a higher correlation value is the language related signal. Further, in this instance, in order to facilitate recognition that the representative signal 601 is the language related signal, it can be possible after the correlation value calculation to change the color of the representative signal 601 having the highest correlation value, for example, in red and to display the same. Thereby a user can recognize at a glance the language related signal.

As has been already explained above, on the screen showing the representative signals 601, 602 and 603, for the respective representative signals, the calculation results of the weights of every channel are displayed in bar graphs. Accordingly, after observing the weights for the respective channels corresponding to the representative signal 601 serving as the language related signal, the operator specifies a channel having the highest weight (step 206). The channel having the highest weight corresponds to an active portion in the brain where responds most to the language task. In the illustrated example, it is understood that the eighth channel shows the highest weight. Thereby, it is diagnosed that the active portion in the brain where responds most to the language task is at a position of the eighth channel on the left temporal lobe. With regard to the bar graph display of the weights, it is also possible to facilitate recognition if the color of the channel having the highest weight in bar graph is changed from that of the other channels, for example, the channel having the highest weight in bar graph is colored in red, alternatively, only the channel having the highest weight in bar graph is displayed by inverting black and white. Further, it will be preferable to display an image showing an attachment state of the probe as shown in FIG. 3 in a window and to apply to the concerned channel the above referred to recognizable indication. Still further, these easy recognizable indications can be realized by softwares assembled in the control portion 31.

According to the present embodiment as has been explained, after being displayed the hemoglobin variation signals measured (after step 202), by clicking "Calc PCA" button displayed on the same screen, since the extraction of the representative signals, the display of the representative signals and the weights and the display of the task related signal determined from correlation with the predetermined language reference and response signal are performed, through observing the weights of the respective channels for the task related signal, the active portion where responds most to the task can easily identified.

Now, when identifying an active portion in the brain not being limited to the identification of the language area region, it is sometimes necessary to know which is dominance right hemisphere or left hemisphere. The living body photometric apparatus according to the present embodiment can be provided with a function of determining such hemispheric dominance.

Figure 2:
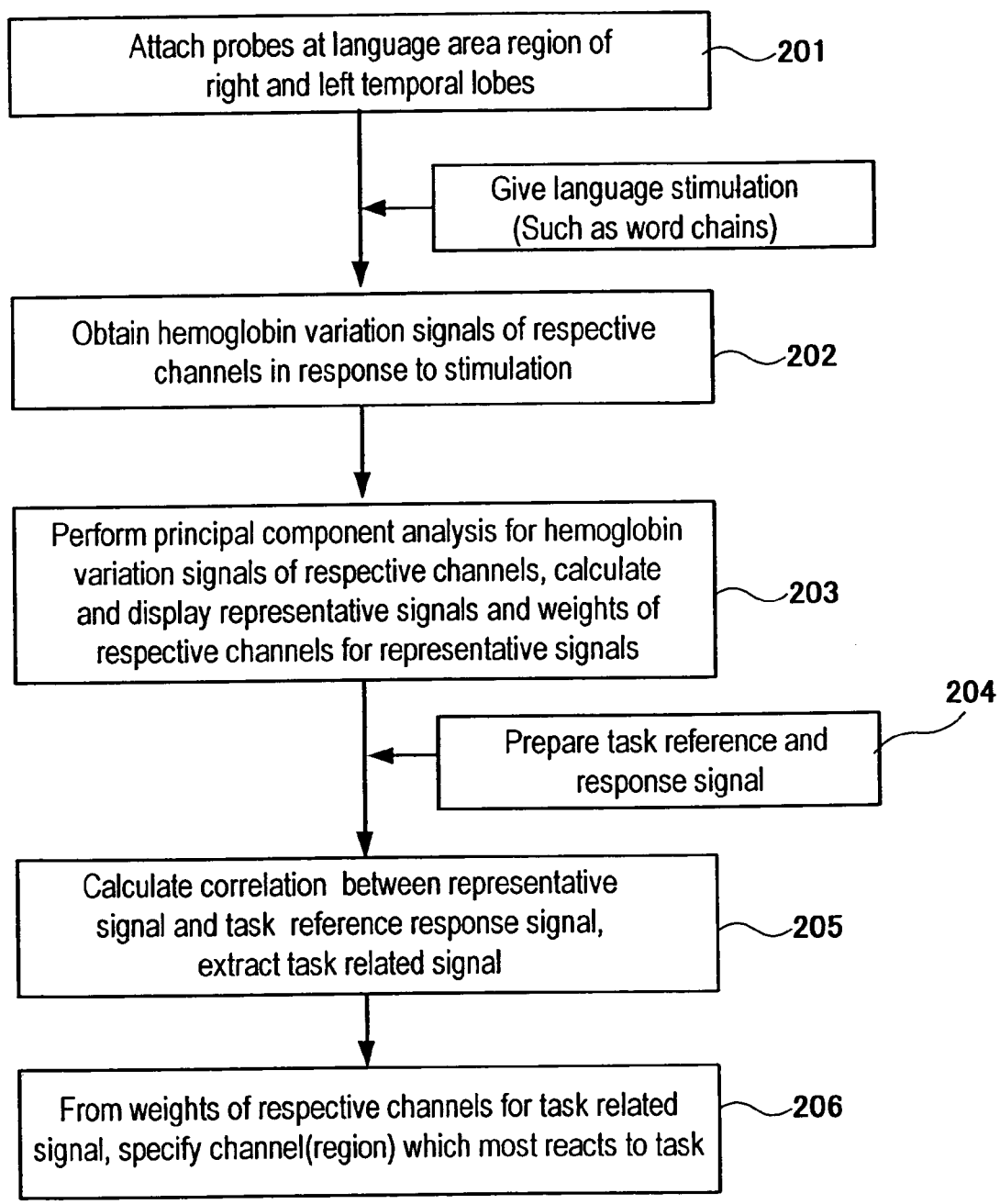
FIG. 2 is a flowchart of language area region identification diagnosis performed by the living body photometric apparatus according to the present invention.
Figure 8:
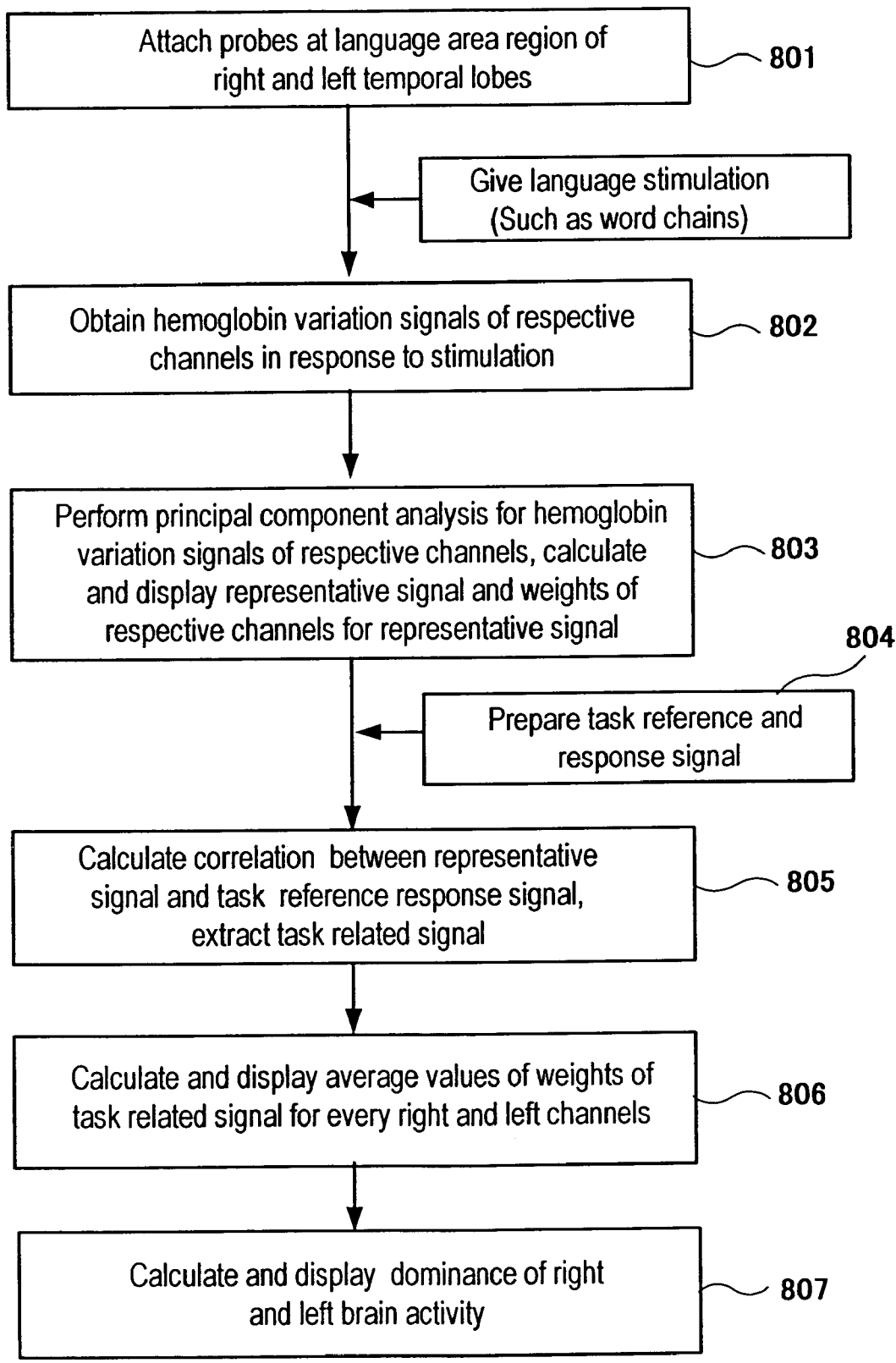
FIG. 8 is a flowchart of dominance hemisphere identification performed by the living body photometric apparatus according to the present invention.

A flowchart of determining the hemispheric dominance is shown in FIG. 8, in which steps 801~805 are equivalent to the steps 201~205 in FIG. 2. Namely, the probes are attached to the right and left temporal lobes where the language area exists (step 801), while giving a task to a subject under a predetermined condition, hemoglobin variation signals of the respective channels are measured (step 802). Subsequently, the principal component analysis is performed for the hemoglobin variation signals of the respective channels, the representative signals are calculated as well as inherent vector values of the respective channels calculated through the principal component analysis are displayed as weights (abundance frequency) of the respective channels for the representative signals (step 803). Subsequently, for the representative signals calculated in step 803, like FIG. 2 embodiment, a correlation with the task reference and response waveform (produced at step 804), which is a typical response pattern to the task is calculated and the task related signal is extracted (step 805).

When the task related signal (a representative signal having the highest correlation value calculated) is extracted in the above manner, average values of the weights of every right and left channels for the task related signals are determined. The average values thus determined are displayed, for example, as shown in FIG. 6, in numerical values at the bottom of the bar graphs showing the weights of the respective channels (step 806). In the example as illustrated, the average value of the weights of the channels 1~12 in the left hemisphere is 0.25 and the average value of the weights of the channels 1~12 in the right hemisphere is 0.125. Further, in the present example, although the average values of the weights of every channels are calculated, it is possible to calculate and display such as average values of absolute value weights, average values of only positive symbol weights or negative symbol weights and average values of weights of above or below a predetermined threshold value.

The hemispheric dominance LI (Laterality Index) of right and left brain activity can be calculated according to equation (1) by making use of the average values 614 and 615 of weights for right and left hemisphere.

$$LI = (Al - Ar)/(Al + Ar) \quad (1)$$

Wherein, Al is the average value of weights for the left hemisphere and Ar is the average value of the weights for the right hemisphere.

The above calculation according to equation (1) is performed either in the signal processing portion 30 or in the control portion (CPU) 31 by making use of a software assembled therein.

The hemispheric dominance LI thus determined, although not illustrated, is displayed, for example, at the center of bar graphs of right and left weights as shown in FIG. 6 as "LI=0.33". This implies that Al>Ar in equation (1), namely, shows that the left hemisphere is dominant, and 0.33 shows including "+" symbol. Oppositely, when Al<Ar in equation (1), it is indicated as "LI=−0.33" by adding "−" symbol to show that the right hemisphere is dominant. Further, the symbols "+" and "−" can be converted into letters "left" and "right" through a software.

In the above explanation, the example in which the measurement was performed after attaching the probes to the right and left temporal lobes and dominance of either the right or left hemisphere was judged, however, it is also possible to further divide the brain active region and to measure the same and then to judge their dominance. Further, in the above explanation, although the identification of language area region was primarily explained, it is also possible to identify regions other than the language area, such as to identify a visual area by giving a subject a visible stimulation as a task.

According to the present invention as has been explained hitherto, through extracting from the measured data only the activity signals in the brain caused by the task (task related signal) and by specifying a channel having the highest correlation with the signal, thereby, the active portion in the brain where responds most to the task can be identified.

Further, according to the present invention, through displaying such as the task related signals and the abundance frequency in the respective channels for the task related signals, a user can easily identify visually the active portion in the brain.

The invention claimed is:

1. A living body photometric apparatus comprising:
   a light source portion for irradiating light beams having predetermined frequencies to a plurality of positions in a measurement region of a subject during an interval including a period when giving a predetermined stimulation task to the subject and a period not giving the same;
   an optical measurement portion for measuring light beams brought about by the irradiated light beams at a position near the light beam irradiation position and for determining measurement data at a plurality of measurement points from the measured light beams;
   a signal processing portion for performing an imaging processing of the measurement data from the optical measurement portion and for calculating from the plurality of measured data at least one stimulation task signal of which a principal component is a signal brought about by the stimulation task given to the subject;
   means for calculating an occupying ratio of the plurality of respective measured data in the stimulation task signal; and
   a displaying means for displaying the stimulation task signal calculated and the calculated occupying ratio of the plurality of respective measured data in the stimulation task signal.

2. A living body photometric apparatus according to claim 1, wherein the light source portion includes a light source for emitting a plurality of light beams having wavelengths near the infrared region of which absorbances with respect to oxy hemoglobin and deoxy hemoglobin in blood of a living body are different, optical modules for modulating differently the wavelengths of the light beams emitted from the light source in the number corresponding to the irradiation positions and irradiation use optical fibers for transmitting the light beams output from the optical modules onto a plurality of different positions of the subject.

3. A living body photometric apparatus according to claim 2, wherein the optical measurement portion includes a plurality of detection use optical fibers which are respectively disposed near the plurality of respective irradiation use optical fibers and guide and transmit the light beams passed inside the subject, a plurality of photo electric converting devices for converting the light beams transmitted by the respective detection use optical fibers into electrical signals, and a signal separation and extraction circuit for determining measurement data of the respective measurement points by making use of output signals of the plurality of photo electric converting devices.

4. A living body photometric apparatus according to claim 1, wherein the stimulation task signal is displayed in a waveform defined by two coordinate axes of signal intensity and time.

5. A living body photometric apparatus according to claim 4, further comprising means for generating a stimulation response and reference pattern in response to the task stimulation of the living body and displaying the same on the displaying means while overlapping on the simulation task signal waveform.

6. A living body photometric apparatus according to claim 5, wherein the stimulation response and reference pattern are stored in a memory means.

7. A living body photometric apparatus according to claim 5 wherein the stimulation response and reference pattern are determined when an operator inputs through an input means data for modifying the pattern with respect to a preset pattern.

8. A living body photometric apparatus according to claim 1, further comprising means for displaying a measurement data having the maximum occupying ratio among the occupying ratios of the respective plurality of measurement data calculated in the stimulation task signal in a discriminable manner from the other measurement data.

9. A living body photometric apparatus according to claim 1, further comprising means for calculating an average value after adding numerical values of the occupying ratios of the respective plurality of measurement data calculated in the stimulation task signal as well as for displaying the calculated average value after the addition on a graph.

10. A living body photometric apparatus according to claim 5, further comprising means for calculating a correlation between the stimulation task signal and the stimulation response and reference pattern and for displaying the calculated correlation value in numerical value near the display positions thereof.

11. A living body photometric apparatus comprising:
a light source portion for irradiating light beams having predetermined frequencies to a plurality of respective positions in right and left temporal lobes of a subject during an interval including a period when giving a predetermined stimulation task to the subject and a period not giving the same;
an optical measurement portion for measuring light beams brought about by the irradiated light beams at a position near the light beam irradiation position and for determining measurement data at a plurality of measurement points from the measured light beams;
a signal processing portion for performing an imaging processing of the measurement data from the optical measurement portion, further for performing principal component analysis for the plurality of measured data and for extracting a representative signal which most reflects a living body reaction when the stimulation task is given;
means for calculating contribution rates of the respective measurement signals with respect to the representative signal;
means for separating the calculated contribution rates of the respective measurement signals for the right and left temporal lobes and for averaging thereof after adding the same; and
a displaying means for displaying the averaged values after addition for the right and left temporal lobes determined by the averaging means after addition in a discriminable manner.

12. A living body photometric apparatus according to claim 11, further comprising a calculating means for calculating hemisphere dominance representing which of the right or left hemisphere in the brain of the subject responds dominantly to the stimulation task by making use of the averaged values after addition for the right and left temporal lobes.

13. A living body photometric apparatus according to claim 12, further comprising means for displaying the hemispheric dominance determined by the calculation means on a display screen of the displaying means.

14. A living body photometric apparatus according to claim 13, wherein the discrimination of the right and left hemispheres is effected by symbols or letters and the degree of the hemispheric dominance is displayed by numerals.

15. A living body photometric apparatus comprising:
a plurality of light source portions, each of the light source portions irradiating light beams having predetermined frequencies to an inside portion of a subject during an interval including a period when giving a predetermined stimulation task to the subject and a period not giving the same;
a plurality of optical measurement portions, each of the optical measurement portions measuring light beams brought about by the irradiated light beams to determine a hemoglobin variation signal in a time course; and
a signal processing portion which calculates from the respective determined hemoglobin variation signals in a time course at a plurality of measurement points defined respectively between the plurality of light source portions and the plurality of optical detection portions, at least one stimulation task signal of which a principal component is a signal brought about by the stimulation task given to the subject, the signal processing portion correlating the calculated at least one stimulation task signal pattern with a reference hemoglobin variation signal pattern selected for the stimulation task and specifying one measurement point among the plurality of the measurement points which responds most to the stimulation by making use of one stimulation task signal in a time course which shows the highest correlation with the reference hemoglobin variation signal in a time course.

16. A living body photometric apparatus according to claim 15, further comprising a means for displaying the reference hemoglobin variation signal pattern in a time course in an overlapping manner with the at least one stimulation task signal in a time course.

17. A living body photometric apparatus according to claim 16, further comprising a memory means which stores the reference hemoglobin variation signal pattern in a time course.

18. A living body photometric apparatus according to claim 16, further comprising an input means through which modification information to a predetermined pattern is inputted to determine the reference hemoglobin variation signal pattern in a time course selected for the predetermined stimulation task.

19. A living body photometric apparatus according to claim 16, wherein the displaying means displays as bars in a bar graph respective occupying ratios of the respective hemoglobin variation signals in a time course at the plurality of measurement points in the at least one stimulation task signal in a time course.

20. A living body photometric apparatus according to claim 19, wherein the displaying means displays a bar in the bar graph representing one measurement point showing the highest occupying ratio in discriminable manner from other bars.

21. A living body photometric apparatus according to claim 19, wherein the displaying means displays an average of a plurality of occupying ratios near the bars of which occupying ratios are averaged in the bar graph.

22. A living body photometric apparatus according to claim 16, wherein the displaying means displays a correlation value of the at least one stimulation task signal pattern in a time course with the reference hemoglobin variation signal pattern in time course selected for the stimulation task near the displayed portion thereof.

23. A living body photometric apparatus according to claim 16, wherein the displaying means displays one of the at least one stimulation task signal patterns in a time course showing the highest correlation value in a different color from another of the at least one other stimulation task signal patterns.

24. A living body photometric apparatus according to claim 20, wherein the displaying means displays a bar in the bar graph representing one measurement point showing the highest occupying ratio in a different color from that of the other bars.

25. A living body photometric apparatus comprising:
 a plurality of light source portions, each of the light source portions irradiating light beams having predetermined frequencies to an inside portion of a subject during an interval including a period when giving a predetermined stimulation task to the subject and a period not giving the same;
 a plurality of optical measurement portions, each of the optical measurement portions measuring light beams brought about by the irradiated light beams to determine a hemoglobin variation signal in a time course;
 a signal processing portion which performs image processing of the respective determined hemoglobin variation signals in a time course at a plurality of measurement points defined respectively between the plurality of light source portions and the plurality of optical detection portions, the signal processing portion extracts a representative signal which most reflects a living body reaction when the stimulation task is given to the subject by subjecting the respective determined hemoglobin variation signals to a principal component analysis, the signal processing portion correlating the extracted representative signal pattern in a time course with a reference hemoglobin variation signal pattern selected for the stimulation task and specifying one measurement point among the plurality of the measurement points which responds most to the stimulation by making use of the representative signal which shows the highest correlation with the reference hemoglobin variation signal in a time course; and
 a display means which displays the signals at least one of the signals processed and extracted by the signal processing portion.

* * * * *